(12) United States Patent
Mikhail et al.

(10) Patent No.: US 12,376,787 B2
(45) Date of Patent: Aug. 5, 2025

(54) BONE FIXATION MONITORING SYSTEM

(71) Applicant: Depuy Synthes Products, Inc., Raynham, MA (US)

(72) Inventors: George Mikhail, Chester Springs, PA (US); Glen Pierson, West Chester, PA (US); Jochen Walser, Zuchwil (CH); Jacob Marks, Raynham, MA (US); Jared Schneider, Raritan, NJ (US); Christopher Shane, West Chester, PA (US)

(73) Assignee: Depuy Synthes Products, Inc., Raynham, MA (US)

( * ) Notice: Subject to any disclaimer, the term of this patent is extended or adjusted under 35 U.S.C. 154(b) by 733 days.

(21) Appl. No.: 17/381,887

(22) Filed: Jul. 21, 2021

(65) Prior Publication Data
US 2022/0022807 A1    Jan. 27, 2022

Related U.S. Application Data

(60) Provisional application No. 63/054,557, filed on Jul. 21, 2020.

(51) Int. Cl.
*A61B 5/00* (2006.01)
*A61B 5/0205* (2006.01)
(Continued)

(52) U.S. Cl.
CPC .......... *A61B 5/4504* (2013.01); *A61B 5/0022* (2013.01); *A61B 5/0031* (2013.01);
(Continued)

(58) Field of Classification Search
CPC ..... A61B 5/4504; A61B 5/0031; G16H 50/20
See application file for complete search history.

(56) References Cited

U.S. PATENT DOCUMENTS

| 1,032,109 A | 7/1912 | Buckingham |
|---|---|---|
| 3,942,535 A | 3/1976 | Schulman |

(Continued)

FOREIGN PATENT DOCUMENTS

| EP | 3355437 A1 | 8/2018 |
|---|---|---|
| WO | WO2000074747 A1 | 12/2000 |
| WO | WO2012005603 A1 | 1/2012 |
| WO | WO2019045681 A1 | 3/2019 |

OTHER PUBLICATIONS

Guillaume Crinon, Pre Tune if Fixed Environment, Article published on LinkedIn, Aug. 22, 2017, 4 pages.
(Continued)

*Primary Examiner* — Daniel L Cerioni
(74) *Attorney, Agent, or Firm* — Flaster Greenberg P.C.

(57) ABSTRACT

A system for monitoring the ossification of an internally fixated fracture in a bone of a subject includes an implantable fixation device and an external wireless reader operative to transmit relative load data experienced by a bone plate across a fracture to a data server where trends in the change in added bone-support provided by the bone plate may be visualized. The implantable fixation device includes a primary load sensor and a reference load sensor, where a load value from the reference load sensor may be used to normalize the load value from the primary load sensor. The external wireless reader is in wireless communication with the implantable fixation device and is operative to receive a signal indicative of the load from each load sensor and to energize each load sensor via inductive charging.

13 Claims, 9 Drawing Sheets

(51) Int. Cl.
*A61B 5/021* (2006.01)
*A61B 5/07* (2006.01)
*A61B 5/103* (2006.01)
*A61B 17/80* (2006.01)
*G16H 10/60* (2018.01)
*G16H 40/67* (2018.01)
*G16H 50/20* (2018.01)
*G16H 50/30* (2018.01)
*G16H 50/50* (2018.01)
*G16H 50/70* (2018.01)

(52) U.S. Cl.
CPC .......... *A61B 5/0205* (2013.01); *A61B 5/021* (2013.01); *A61B 5/076* (2013.01); *A61B 5/103* (2013.01); *A61B 5/486* (2013.01); *A61B 5/4866* (2013.01); *A61B 5/7275* (2013.01); *A61B 5/742* (2013.01); *A61B 5/746* (2013.01); *A61B 17/80* (2013.01); *G16H 10/60* (2018.01); *G16H 40/67* (2018.01); *G16H 50/20* (2018.01); *G16H 50/30* (2018.01); *G16H 50/50* (2018.01); *G16H 50/70* (2018.01); *A61B 2562/0252* (2013.01); *A61B 2562/0261* (2013.01)

(56) References Cited

U.S. PATENT DOCUMENTS

| | | | |
|---|---|---|---|
| 5,324,315 A | 6/1994 | Grevious | |
| 5,350,413 A | 9/1994 | Miller | |
| 5,446,447 A | 8/1995 | Carney et al. | |
| 5,702,431 A | 12/1997 | Wang et al. | |
| 5,704,352 A | 1/1998 | Tremblay et al. | |
| 5,725,578 A | 3/1998 | Knapp et al. | |
| 5,833,603 A | 11/1998 | Kovacs et al. | |
| 6,088,619 A | 7/2000 | Hein et al. | |
| 6,708,065 B2 | 3/2004 | Von Arx et al. | |
| 7,072,718 B2 | 7/2006 | Von Arx et al. | |
| 7,079,900 B2 | 7/2006 | Greenburg et al. | |
| 7,187,978 B2 | 3/2007 | Malek et al. | |
| 7,228,175 B2 | 6/2007 | Jain et al. | |
| 7,256,695 B2 | 8/2007 | Hamel et al. | |
| 7,286,881 B2 | 10/2007 | Schommer et al. | |
| 7,392,092 B2 | 6/2008 | Li et al. | |
| 7,483,752 B2 | 1/2009 | Von Arx et al. | |
| 7,486,048 B2 | 2/2009 | Tsukamoto et al. | |
| 7,701,878 B2 | 4/2010 | Mora | |
| 7,774,069 B2 | 8/2010 | Olson et al. | |
| 7,786,867 B2 | 8/2010 | Hamel et al. | |
| 7,878,207 B2 | 2/2011 | Goetz et al. | |
| 7,932,696 B2 | 4/2011 | Peterson | |
| 8,140,168 B2 | 3/2012 | Olson et al. | |
| 8,188,619 B2 | 5/2012 | Azancot et al. | |
| 8,195,305 B2 | 6/2012 | Nghiem et al. | |
| 8,311,638 B2 | 11/2012 | Aghassian | |
| 8,369,959 B2 | 2/2013 | Meskens | |
| 8,386,048 B2 | 2/2013 | McClure et al. | |
| 8,416,088 B2 | 4/2013 | Ortega et al. | |
| 8,439,821 B2 | 5/2013 | Stiller et al. | |
| 8,463,392 B2 | 6/2013 | Aghassian | |
| 8,463,394 B2 | 6/2013 | Forsell | |
| 8,473,066 B2 | 6/2013 | Aghassian et al. | |
| 8,498,713 B2 | 7/2013 | McClure et al. | |
| 8,502,675 B2 | 8/2013 | Hamel et al. | |
| 8,509,909 B2 | 8/2013 | Figueiredo et al. | |
| 8,612,013 B2 | 12/2013 | Forsell | |
| 8,700,175 B2 | 4/2014 | Fell | |
| 8,755,899 B2 | 6/2014 | Von Arx et al. | |
| 8,798,756 B2 | 8/2014 | McClure et al. | |
| 8,938,305 B2 | 1/2015 | Abrahamson et al. | |
| 8,965,523 B2 | 2/2015 | Forsell | |
| 9,042,985 B2 | 5/2015 | Marsh et al. | |
| 9,089,717 B2 | 7/2015 | Forsell | |
| 9,095,709 B2 | 8/2015 | McClure et al. | |
| 9,108,056 B2 | 8/2015 | McClure et al. | |
| 9,125,242 B2 | 9/2015 | Budgett | |
| 9,205,269 B2 | 12/2015 | Marsh et al. | |
| 9,227,075 B2 | 1/2016 | Aghassian et al. | |
| 9,240,633 B2 | 1/2016 | Shi et al. | |
| 9,339,660 B2 | 5/2016 | Feldman et al. | |
| 9,381,354 B2 | 7/2016 | Roy et al. | |
| 9,446,254 B2 | 9/2016 | Ozawa et al. | |
| 9,526,895 B2 | 12/2016 | McClure et al. | |
| 9,533,162 B2 | 1/2017 | Ter-Petrosyan et al. | |
| 9,536,656 B2 | 1/2017 | Oettinger et al. | |
| 9,597,516 B2 | 3/2017 | Lee et al. | |
| 9,764,134 B2 | 9/2017 | McClure et al. | |
| 9,792,469 B1 | 10/2017 | Park | |
| 9,821,160 B2 | 11/2017 | Roy et al. | |
| 9,825,471 B2 | 11/2017 | Hansen | |
| 9,872,997 B2 | 1/2018 | Angara et al. | |
| 9,878,170 B2 | 1/2018 | Angara et al. | |
| 9,887,574 B2 | 2/2018 | Angara et al. | |
| 9,913,990 B2 | 3/2018 | Ter-Petrosyan et al. | |
| 9,919,156 B2 | 3/2018 | McClure et al. | |
| 9,997,928 B2 | 6/2018 | Petersen et al. | |
| 10,016,602 B2 | 7/2018 | Khalil et al. | |
| 10,052,481 B2 | 8/2018 | McClure et al. | |
| 10,194,802 B2 | 2/2019 | Windolf | |
| 10,199,884 B2 | 2/2019 | Angara et al. | |
| 10,226,637 B2 | 3/2019 | Aghassian et al. | |
| 10,285,641 B2 | 5/2019 | Kang et al. | |
| 10,311,662 B2 | 6/2019 | Westby et al. | |
| 10,362,982 B2 | 7/2019 | Stevenson et al. | |
| 10,363,426 B2 | 7/2019 | Aghassian et al. | |
| 10,413,738 B2 | 9/2019 | Ter-Petrosyan et al. | |
| 10,525,181 B2 | 1/2020 | Petersen | |
| 10,603,501 B2 | 3/2020 | Aghassian et al. | |
| 10,617,880 B2 | 4/2020 | Zellmer et al. | |
| 10,625,078 B2 | 4/2020 | McClure et al. | |
| 10,632,318 B2 | 4/2020 | Stouffer | |
| 10,665,043 B2 | 5/2020 | Westby et al. | |
| 10,665,044 B2 | 5/2020 | Westby et al. | |
| 10,665,045 B2 | 5/2020 | Westby et al. | |
| 10,665,046 B2 | 5/2020 | Westby et al. | |
| 2005/0113887 A1 | 5/2005 | Bauhahn et al. | |
| 2005/0222624 A1 | 10/2005 | Greenberg et al. | |
| 2006/0235485 A1 | 10/2006 | Ok et al. | |
| 2008/0154337 A1 | 6/2008 | McClure et al. | |
| 2008/0262376 A1 | 10/2008 | Price | |
| 2009/0259273 A1 | 10/2009 | Figueiredo et al. | |
| 2011/0004076 A1* | 1/2011 | Janna | H01Q 1/02 600/302 |
| 2011/0098603 A1 | 4/2011 | Deirmengian et al. | |
| 2011/0291490 A1* | 12/2011 | Shi | H01Q 1/52 307/104 |
| 2012/0065548 A1* | 3/2012 | Morgan | A61B 5/4504 600/587 |
| 2013/0190654 A1* | 7/2013 | Deirmengian | A61B 17/80 600/587 |
| 2016/0051192 A1* | 2/2016 | Kang | A61B 5/0205 600/300 |
| 2016/0198981 A1 | 7/2016 | Demir et al. | |
| 2016/0310077 A1 | 10/2016 | Hunter et al. | |
| 2017/0361115 A1 | 12/2017 | Aghassian et al. | |
| 2017/0361116 A1 | 12/2017 | Aghassian et al. | |
| 2018/0055444 A1 | 3/2018 | Windolf | |
| 2018/0078329 A1 | 3/2018 | Hansen et al. | |
| 2018/0345025 A1 | 12/2018 | Stinauer et al. | |
| 2019/0009097 A1 | 1/2019 | Hartley et al. | |
| 2019/0038214 A1 | 2/2019 | Mikhail et al. | |
| 2019/0261888 A1* | 8/2019 | Zdeblick | A61B 5/02416 |
| 2020/0138361 A1* | 5/2020 | Amiot | A61B 5/746 |
| 2020/0397639 A1* | 12/2020 | Mason | A63B 21/4049 |
| 2020/0405150 A1* | 12/2020 | Trabish | A61B 5/0031 |

OTHER PUBLICATIONS

Marmor Meir T et al: "Biomedical research models in the science of fracture healing—Pitfalls & promises", Injury, John Wright and Sons, Bristol, GB, vol. 51, No. 10, Jun. 15, 2020 (Jun. 15, 2020), pp.

(56) References Cited

OTHER PUBLICATIONS 2118-2128, XP086259424, ISSN: 0020-1383, DOI: 10.101 6/J. INJURY.2020.06.025.

* cited by examiner

FIG. 8

BONE FIXATION MONITORING SYSTEM

CROSS-REFERENCE TO RELATED APPLICATIONS

The present application claims the benefit of priority from U.S. Provisional Patent No. 63/054,557, filed Jul. 21, 2020, which is incorporated by reference in its entirety.

TECHNICAL FIELD

The present disclosure relates generally to a system and method for monitoring the healing/ossification of a fractured bone.

BACKGROUND

Conventional bone fixation systems include a bone plate having screw holes that receive fixation members, such as screws that are configured to attach to underlying bone that includes, at a minimum, a pair of bone segments separated by a bone gap. The bone gap can be a fracture created by a traumatic event, an osteotomy, or can be the result of debridement of a joint of two discrete bones to be joined in an arthrodesis. Thus, the bone plate can be affixed to the bone on opposed sides of the bone gap via the bone screws to promote union of the bone segments (e.g., healing of the fracture or ossification of the joint). Bone fixation systems can further include temporary Kirschner wires (K-wires) that are temporarily inserted into apertures of the bone fixation plate and into the underlying bone segments to determine proper length, rotation and alignment of the bone segments prior to permanent plate fixation. Once the bone fixation plate has been properly positioned, the permanent bone screws can be inserted into one or more bone screw holes on opposed sides of the bone gap and affixed to the underlying bone.

SUMMARY

A system for monitoring the ossification of an internally fixated fracture in a bone of a subject includes an implantable fixation device and an external wireless reader. The external wireless reader is operative to transmit relative load data experienced by a bone plate across a fracture to a data server where trends in the change in added bone-support provided by the bone plate may be visualized.

The implantable fixation device includes a primary load sensor and a reference load sensor, both in direct physical contact with a bone plate. The primary load sensor is provided on the bone plate at a first location that is operative to be positioned directly adjacent to the fracture. The primary load sensor may generally include a first strain sensor operative to monitor an amount of strain in the bone plate at the first location (a Primary Strain) and communication circuitry operative to transmit a first wireless signal indicative of the amount of Primary Strain. The reference load sensor is provided on the bone plate at a second location that is spaced apart from the first location. The reference load sensor may include a second strain sensor operative to monitor an amount of strain in the bone plate at the second location (a Reference Strain) and communication circuitry operative to transmit a second wireless signal indicative of the amount of Reference Strain.

The external wireless reader may receive the first and second wireless signals via an antenna, determine an amount of relative support provided by the bone plate as a result of the fracture using the received indication of the Primary Strain and the received indication of the Reference Strain, and transmit the determined amount of relative support to a data server over a wireless communication network using a wireless communications radio. In one configuration, the amount of relative support provided by the bone plate as a result of the fracture may be computed by dividing the Primary Strain value by the Reference Strain value.

Using these devices, a method of acquiring bone ossification data from an implantable smart fixation device provided within a subject may begin by energizing an extracorporeal antenna provided with the external wireless reader to generate an alternating magnetic field and inductively energize each of the primary load sensor and reference load sensor. The external wireless reader may then receive a wireless data signal from each load sensor, the wireless data signal indicative of an amount of strain experienced by the bone plate at that respective location.

Further, a method of monitoring bone fracture ossification from a plurality of subjects via a data server may begin by receiving, via a wireless communication network, a plurality of bone ossification data points from a plurality of subjects. Each data point represents a measurement taken from a smart fixation device secured to a bone of a subject across a fracture. The measurement represents an amount of load carried the fixation device across the fracture relative to an amount of load carried by the fixation device at solid bone. The method further includes storing each of the plurality of data points in nonvolatile memory in connection with the date and time that the measurement was taken and with a patient identifier representing the source of the measurement. The data server may then provide a physician interface to graphically illustrate a change in measurements over time from each of a plurality of different subjects.

In one configuration, the data server may maintain a machine learning predictive model that generates a predicted patient specific healing trajectory for each subject. The patient specific healing trajectory including a predicted trajectory and a confidence interval that represents a likely course of healing progression beginning at the time of bone fixation. The method further includes overlaying the plurality of data points or empirical trendline for a subject on a graphical representation of the predicted patient specific healing trajectory within the physician interface. The machine learning predictive model may be refined using at least a subset of the received plurality of data points and a plurality of secondary factors including at least two of: a nature and location of the fracture, the subject's height, weight, age, sex, metabolic profile, blood pressure, pre-existing conditions, complicating risk factors, or comorbidities.

The data server may further compute a forward-looking healing trajectory for each subject that extending forward in time from the most recently acquired data point for that subject. This forward-looking healing trajectory may also be overlaid on the graphical representation of the predicted patient specific healing trajectory. The data server may provide an alert via the physician interface if one of the data points or the forward-looking healing trajectory is outside of the confidence interval.

As used herein, the terms "a," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

BRIEF DESCRIPTION OF THE DRAWINGS

FIG. 8 is a schematic illustration of a physician interface that may display patient-specific healing trendlines constructed for one or more patients.

DETAILED DESCRIPTION

The present technology generally relates to a system and device that enable a physician to better understand the recovery and healing process of an internally fixated bone fracture than is available with more traditional forms of treatment. More specifically, the present designs provide for regular (even daily) testing of the healing progress of the fracture, while providing the convenience of performing the testing outside the confines of a clinic or exam room. Through the use of connected hardware and a centralized data management system, an orthopedic physician may gain remote access to acquired diagnostic data that is drawn directly from the internal fixation system. Using this quantitative data, the physician may be better equipped to counsel a patient, for example, in a virtual, telemedicine-based manner. In such a manner, the present technology may make remote monitoring the requested standard of care for monitoring the healing progress of an internally fixated bone fracture.

Figure 1:
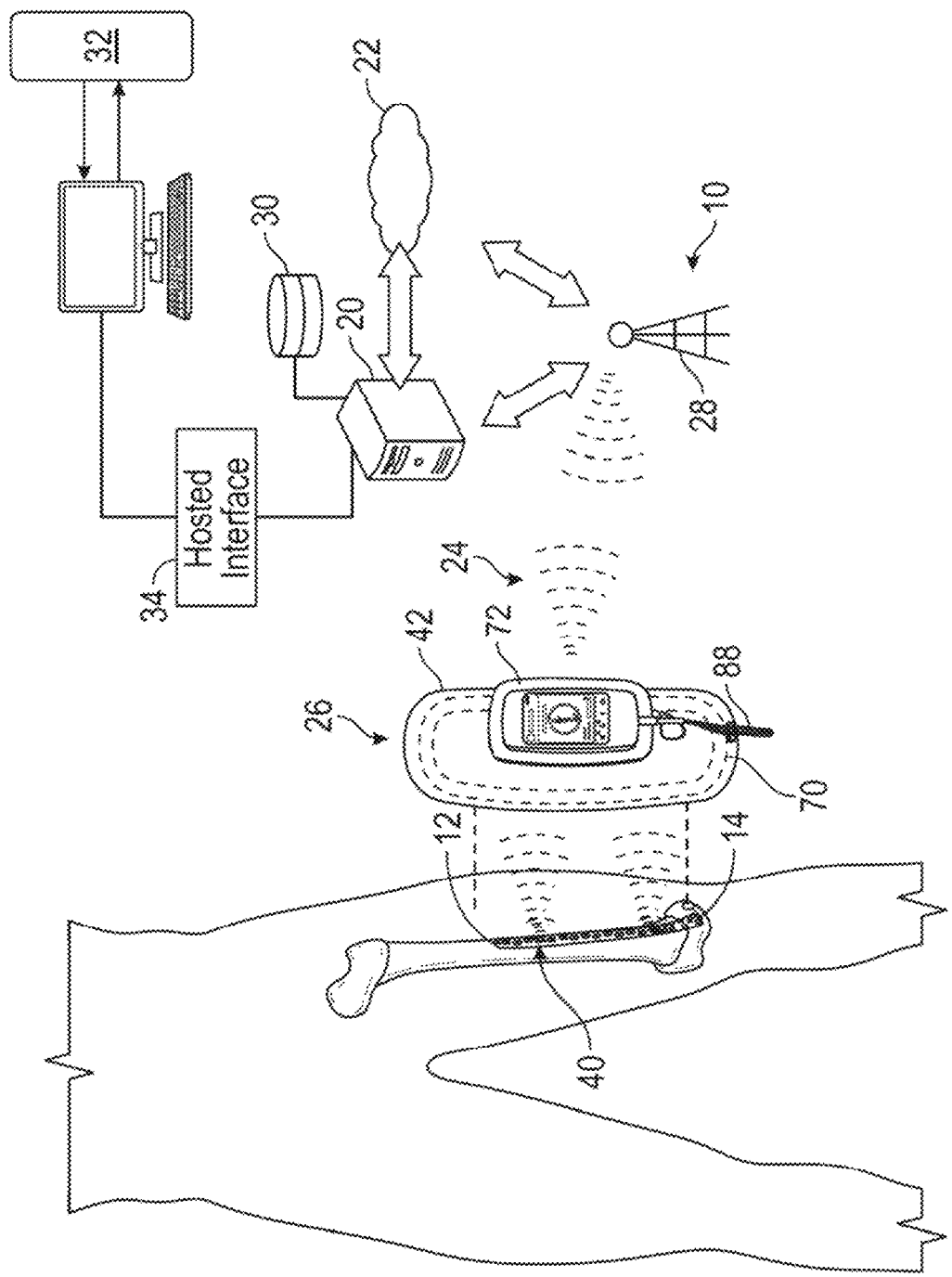
FIG. 1 is a schematic diagram of a system for monitoring the healing of a bone fracture.
Figure 2:
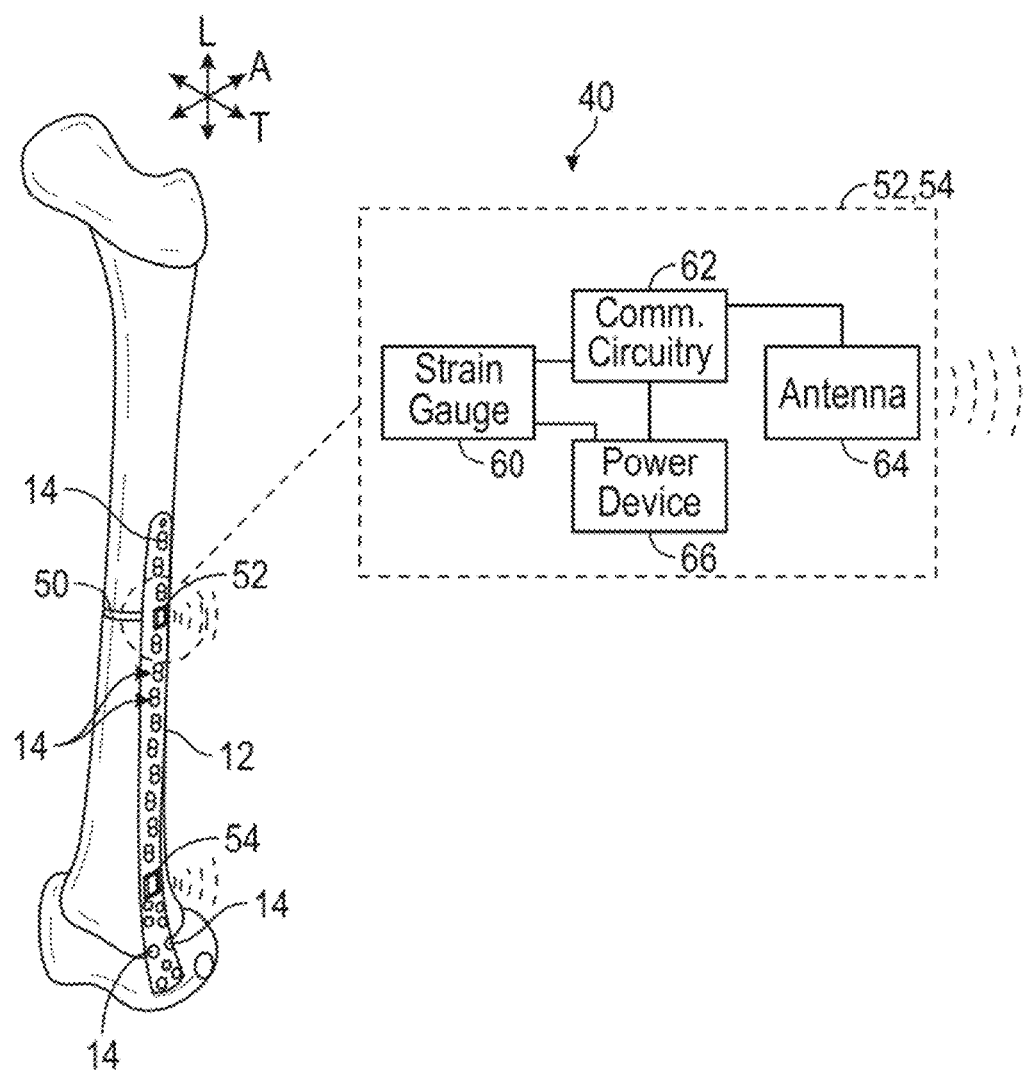
FIG. 2 is a schematic diagram of an implantable smart fixation device for surgically repairing a fractured bone.

Referring to the drawings, wherein like reference numerals are used to identify like or identical components in the various views, FIG. 1 schematically illustrates a system 10 for remotely monitoring the healing/ossification of a bone fracture or other bone joint that is internally fixated with a bone plate 12 and plurality of permanent fixation members such as bone screws 14 (as better shown in FIG. 2). In general, the present system 10 includes a data server 20 and/or cloud computing system 22 that is operative to receive patient data 24 from one or more patient monitoring systems 26 across a wireless communication network 28. The data server 20/cloud computing system 22 may store the received patient data 24 in an associated non-volatile memory/database 30 and may visually present this data to a medical professional 32 via a hosted physician interface 34. The patient monitoring system 26 may be configured to periodically monitor the amount of load carried by the bone plate 12 across the fracture throughout the duration of the healing process. This load measurement may be normalized against loads carried by the bone plate 12 away from the fracture and may be periodically transmitted from the patient monitoring system 26 to the data server 20 where it may be aggregated with other patient data 24 to highlight trends in the healing of the fracture.

With continuing reference to FIG. 1, the data server 20 may be implemented as one or more high-speed server computers or mainframe computing devices capable of handling bulk data processing and data visualization tasks. The cloud computing system 22, on the other hand, may operate as middleware for IoT (Internet of Things), WoT (Web of Things), and/or M2M (machine-to-machine) services, connecting an assortment of heterogeneous electronic devices with a service-oriented architecture (SOA) via a data network. As an example, cloud computing system 22 may be implemented as a middleware node to provide different functions for dynamically onboarding heterogeneous devices, multiplexing data from each of these devices, and routing the data through reconfigurable processing logic for processing and transmission to one or more destination applications. The wireless communication network 28 may be any available type of network, including a combination of public distributed computing networks (e.g., Internet) and secured private networks (e.g., local area network, wide area network, virtual private network). It may also include wireless and wireline transmission systems (e.g., satellite, cellular network, terrestrial networks, etc.). Most if not all data transaction functions may be conducted, for example, over a wireless network, such as a wireless local area network (WLAN) or cellular data network operating, for example, according to a 4G, 5G, LTE, LPWAN, LTE-M, CAT-M1, or NB-IoT protocol.

As further illustrated in FIG. 1, the patient monitoring system 26 generally includes an implantable smart fixation device 40 and an external (extracorporeal) wireless reader 42 for interfacing with the smart fixation device 40. The external wireless reader 42 is configured to wirelessly receive data from the smart fixation device 40 through the skin of the patient, for example, via a radio frequency (RF) data communication means such as RFID or NFC. In at least some embodiments, the external wireless reader 42 may further be configured to wirelessly provide a source of power to the smart fixation device 40, which may enable the fixation device 40 to not require internal batteries to operate.

Referring to FIG. 2, the implantable smart fixation device 40 may include a rigid bone plate 12 that is configured to be secured across and to opposing sides of a bone fracture 50 using plurality of permanent fixation members such as bone screws 14. The bone plate 12 can be formed from any suitable implantable material such as, without limitation, a metal (e.g., a titanium alloy) or a polymer such as polyether ether ketone (PEEK). While the present disclosure generally discusses the use of the remote monitoring technology in connection with a bone plate style fixation device, the present technology may also be utilized with other rigid fixation members, such as implantable rods, pedicle screws, intervertebral implants, and the like.

The smart fixation device 40 may generally include at least one primary load sensor 52 that is operative to sense the load carried by the plate at the fracture 50. As the fracture heals/ossifies, the amount of load carried by the plate 12 at the fracture 50 should decrease (i.e. while the load carrying capacity of the healing bone correspondingly increases). In many embodiments, the smart fixation device may further include at least one reference load sensor 54 that is operative to sense the load carried by the plate 12 at a location that is spaced apart from the fracture. The reference load sensor 54 may generally serve as a baseline for the amount of load carried by the plate 12 adjacent to healthy or unfractured bone.

In one configuration, each load sensor 52, 54 may include one or more strain gauges 60 that have an electrical property that varies in an established manner with an amount of strain experienced by the gauge/plate at that location. Examples of suitable strain gauges include resistive strain gauges, capacitive strain gauges, piezoelectric materials, electroactive polymer materials, and the like. Each strain gauge 60 may be held in firm, rigid contact with the plate 12 such that any bending or flexure of the plate is also experienced by the gauge. As is well established, strain and load are directly proportional and thus measuring strain is one way of monitoring the load carried by the plate.

With continued reference to FIG. 2, the smart fixation device 40 further includes communication circuitry 62 that is electrically coupled with each strain gauge 60, and an antenna 64 in communication with the communication circuitry 62. The communication circuitry 62 is configured to receive the measurement value from the strain gauge 60 and provide the measurement value to the antenna 64 in a suitable form for wireless transmission. The communication circuitry 62 can include a wireless transmitter or transponder that receives the measurement value from the strain gauge 60 and prepares the measurement value for wireless transmission. For example, the communication circuitry 62 can include processing components such as (without limitation) one or more of (i) memory configured to store the measurement value, (ii) a digital-to-analog converter configured to convert the measurement value to analog format, (iii) a radio-frequency (RF) modulator configured to modulate the measurement value, (iv) an error-correction encoder configured to encode the measurement value, and other processing consistent with the wireless technology employed by the system.

In one example, the communication circuitry 62 can be configured as a passive radio-frequency identification (RFID) transponder. Alternatively, the communication circuitry 62 can be configured using any other wireless communication technology suitable for communicating through the skin such as (without limitation) battery-assisted passive RFID, active RFID, Bluetooth, and Wi-Fi. The communication circuitry 62 can further include a unique identifier (ID) that can be used to distinguish each load sensor from other sensors. In one example, the unique ID can be an ID of an RFID tag. The antenna 64 is configured to convert an electrical signal corresponding to the measurement value from the communication circuitry 62 into radio waves so as to transmit the measurement value wirelessly through the patient's skin to the external wireless reader 42 situated outside of the patient's body.

As further illustrated in FIG. 2, the smart fixation device 40 can comprise a power device 66 configured to supply power to the strain gauges 60 and communication circuitry 62. In at least some examples, the power device 66 can include an energy harvesting device configured to capture energy from a suitable energy source that is separate from the smart fixation device 40. For example, the energy source can be radio waves communicated from the external wireless reader 42. Alternatively, the power device 66 can capture energy from the patient's body itself or from another external source such as a source external to the patient's body. More broadly speaking, the energy source can include (without limitation) sensed kinetic energy, electric fields, magnetic fields, and so on. In a preferred embodiment, however, the power device 40 does not include a typical electrochemical battery.

In one configuration, each load sensor 52, 54 may have its own dedicated communication circuitry 62, antenna 64, and/or power device 66 that is local to that respective load sensor (i.e., as an integrated package). In this configuration, the primary load sensor 52 may transmit a first wireless signal indicative of the amount of strain monitored by the primary load sensor 52 (i.e., a primary strain value), while the reference load sensor 54 may simultaneously transmit a second wireless signal indicative of the amount of strain monitored by the reference load sensor 54 (i.e., a reference strain value). In other embodiments, the smart fixation device 40 may have common communication circuitry 62, antenna 64, and/or power device 66 that may be shared across the entire device 40 (i.e., with each load sensor 52, 54 in electrical communication with the shared communication circuitry 62, antenna 64, and/or power device 66). Further embodiments and disclosure of a smart fixation device 40 is provided in US 2019/0038214, which is incorporated by reference in its entirety and for all purposes.

Figure 3:
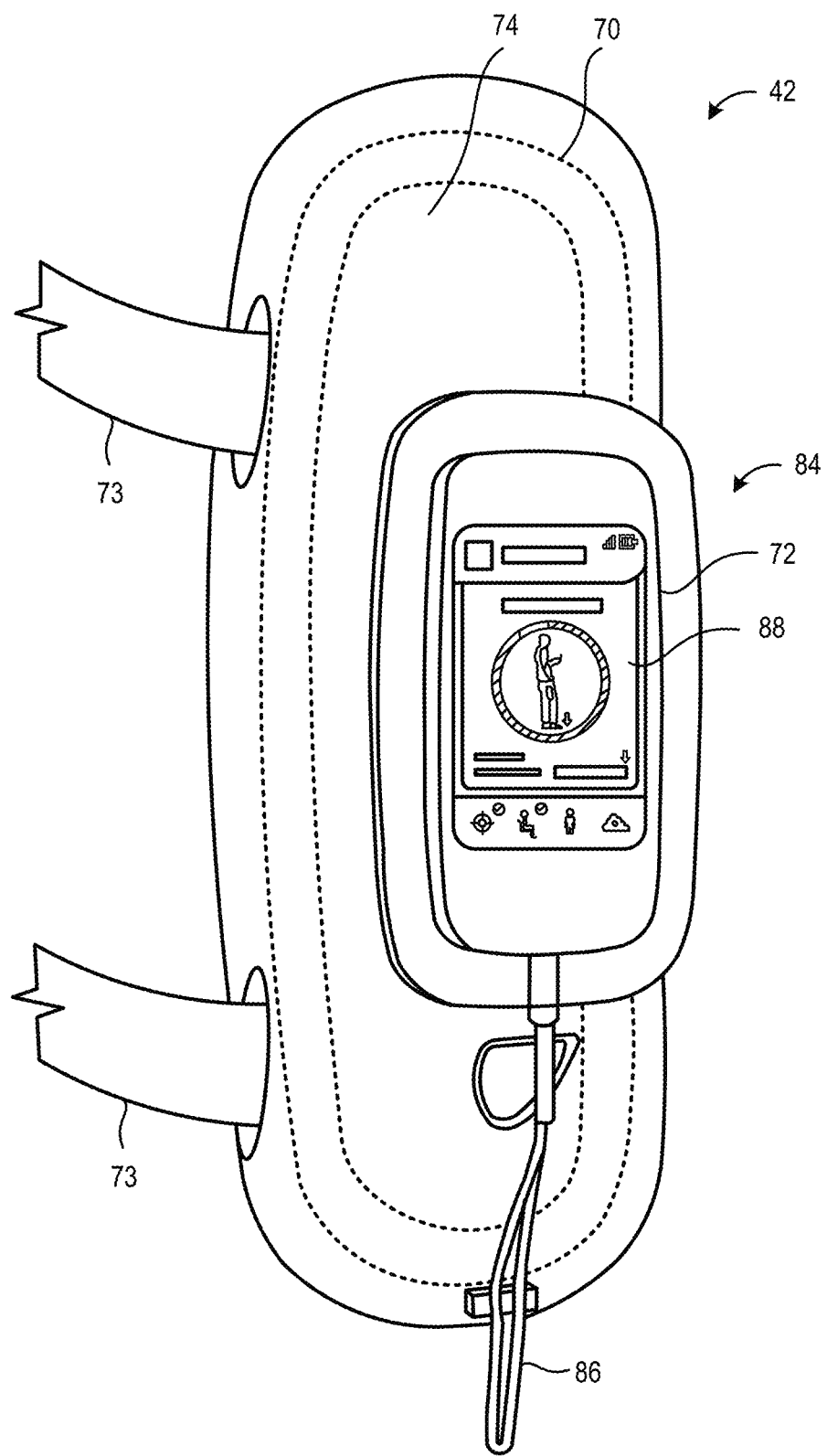
FIG. 3 is a schematic side perspective view of an external wireless reader for wirelessly interfacing with an implantable smart fixation device.

As noted above, the external wireless reader 42 is configured to wirelessly receive data from the smart fixation device 40 through the skin of the patient. To facilitate these communications, as generally shown in FIG. 3, the external wireless reader 42 generally includes one or more antenna 70, such as a Radio Frequency Identification (RFID) antenna, in communication with a portable computing device 72. The antenna 70 may be configured to be attached directly to an external surface of the patient's body or clothing. This attachment may be facilitated by the use of one or more straps 73, harnesses, braces, adhesive patches, elastic sleeves, cuffs, and the like. In one particular embodiment, the antenna 70 may be provided within a flexible fabric carrier 74 that may be particularly suited to contour to the user's body. The antenna 70 may generally comprise a looped coil that has a length adapted to extend parallel to the bone plate 12 and a width adapted to extend transverse to and/or circumferentially around the bone plate 12. The length may control the amount of the plate that the antenna can communicate with, while the width may affect the depth of tissue through which the antenna receives reliable signals. In one configuration, the length of the antenna 70 is greater than the distance between the primary load sensor 52 and the reference load sensor 54. In another configuration, the length of the antenna 70 is at least 10% greater than the distance between the primary load sensor 52 and the reference load sensor 54. In one embodiment, the antenna 70 may have a length of between about 20 cm and about 50 cm, or between about 25 cm and about 40 cm. Likewise, the antenna 70 may have a width of between about 12 cm and about 20 cm or between about 14 cm and about 17 cm.

Figure 4:
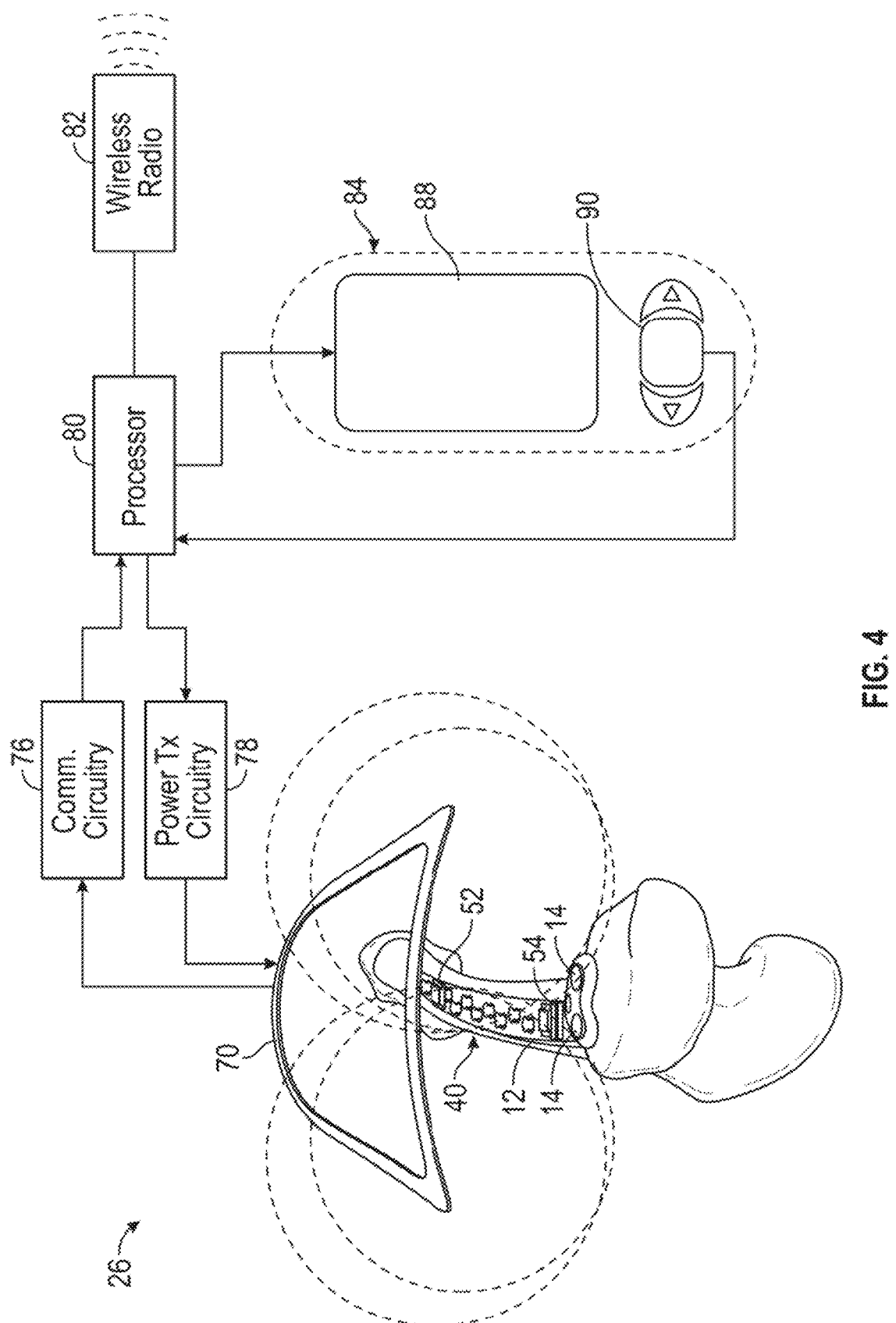
FIG. 4 is a schematic diagram of a portable computing device wirelessly communicating with an implantable smart fixation device via an extracorporeal antenna.

As illustrated in FIG. 4, the portable computing device 72 may include short-range communications circuitry 76 and/or power transmission circuitry 78 in communication with antenna 70. The short-range communications circuitry 76 may be operative to receive digital information from the smart fixation device 40 via the antenna 70. In some embodiments, the short-range communications circuitry 76 may comprise a digital receiver or transceiver such as an RFID transceiver or Near Field Communications (NFC) transceiver. In one configuration, the antenna 70 may operatively communicate with each load sensor 52, 54 simultaneously, for example, through the use of different data transmission frequencies or through the use of differing digital identifiers that are provided with the strain data. The power transmission circuitry 78 can include an inductive charging circuit that is operative to supply electro-magnetic power via the antenna 70 (i.e., an alternating magnetic field) to inductively power the smart fixation device 40.

With continued reference to FIG. 4, the portable computing device 72 may further include a processor 80, a wireless communications radio 82, and a user interface 84. The wireless communications radio 82 may be operative to communicate with and over the wireless communication network 28, and may comprise a BLUETOOTH or BLUETOOTH LOW ENERGY chipset, a Wi-Fi radio operative to digitally communicate using a communications protocol according to the IEEE 802.11, or a cellular radio operative to communicate according to a 4G, 5G, LTE, LPWAN, LTE-M, CAT-M1, NB-IoT protocol, or the like. In some embodiments, the portable computing device 72 may further include a subscriber identity module (SIM) card to facilitate communications over a cellular network.

The processor 80 may be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, and/or signal conditioning and buffering electronics. The processor 80 is configured to execute or perform one or more electronic functions through the execution of software or firmware code stored in non-volatile memory that is accessible by the processor 80. For example, the processor 80 may be capable of executing code that reads one or more strain values from the smart fixation device 40, that selects an average or filtered representative strain value, that communicates with the user via the user interface 84, and/or that communicates over the wireless communication network 28 via the wireless communications radio 82.

The portable computing device 72 may be in communication with the antenna 70 through the use of either a wired or wireless communication link. In one configuration, such as generally shown in FIG. 3, the portable computing device 72 may be electrically coupled to the antenna 70 through the use of a wired tether 86. Such a design may have the benefits of providing a self-contained diagnostic apparatus that only relies on a single power source. More specifically, absent the wired tether 86, the antenna 70 would need a first power source to enable/power communications with both the sensor and the portable computing device 72, while the portable computing device 72 would need a second power source. Coupling the two elements reduces the need for a consumer to maintain sufficient battery levels on two separate devices, while also reducing device complexity. The wired tether 86 also enables the portable computing device 72 to be held in a convenient and accessible location during the data acquisition without the need for a strained posture to view a screen that may otherwise be out of the patient's view. In one configuration, the antenna portion of the device may further include a holster or other securing mechanism for attaching and securing the portable computing device 72 when not in use.

In another embodiment, the portable computing device 72 maybe in wireless communication with the antenna 70 using a suitable wireless protocol. For example, in one configuration, the portable computing device 72 may be a smart phone or tablet device that is in wireless communication with the antenna (and/or communication circuitry provided thereon) using, for example, a Bluetooth protocol.

Figure 5:
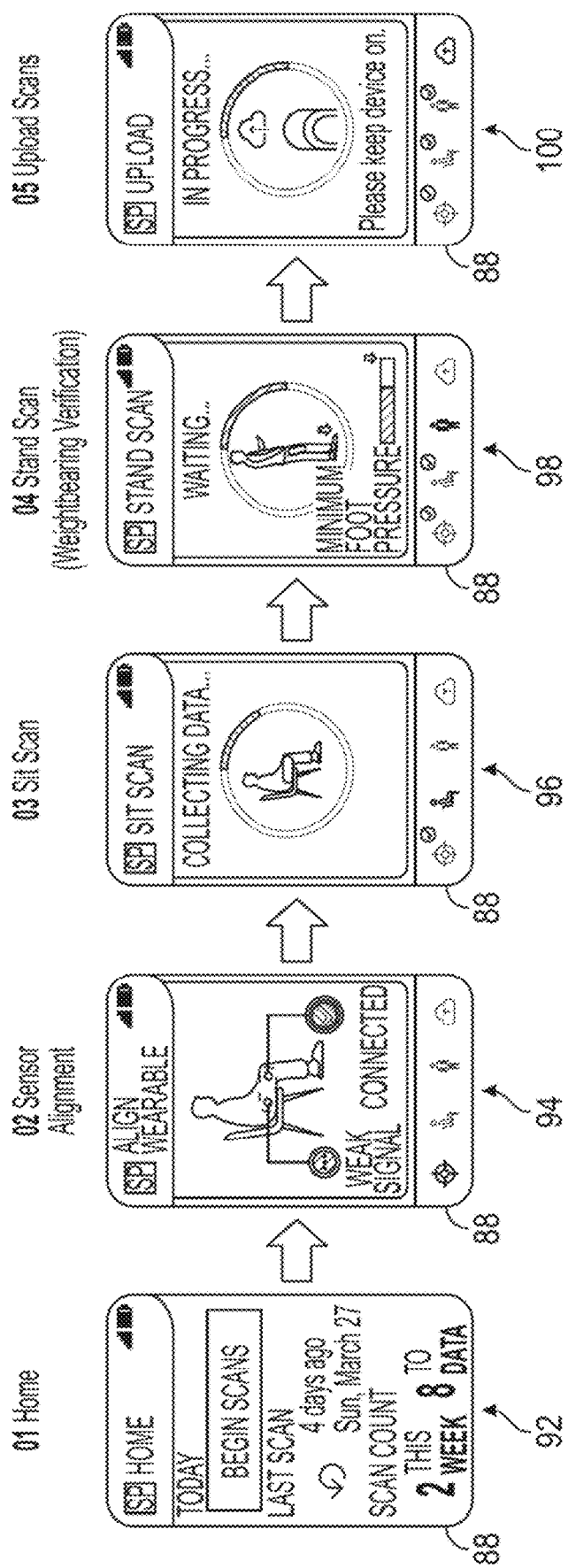
FIG. 5 is a schematic illustration of a progression of user interface display screens that may be displayed to a patient via a portable computing device, such as shown in FIGS. 3-4, during a measurement.

As further illustrated in FIG. 4, the user interface 84 may include a visual display 88, such as an LCD or OLED display, and one or more input devices 90 such as button or touch-screen digitizer. As generally shown in FIG. 5, the display 88 may be operative to provide one or more visual cues to the patient, such as indicating the start of a reading (at 92), verifying sensor alignment (at 94), instructing a posture for and occurrence of a reference measurement (at 96), instructing a posture for and occurrence of a load-bearing measurement (at 98), and/or the uploading of measurement data to the data server/cloud via the wireless communication network 28 (at 100).

Figure 6:
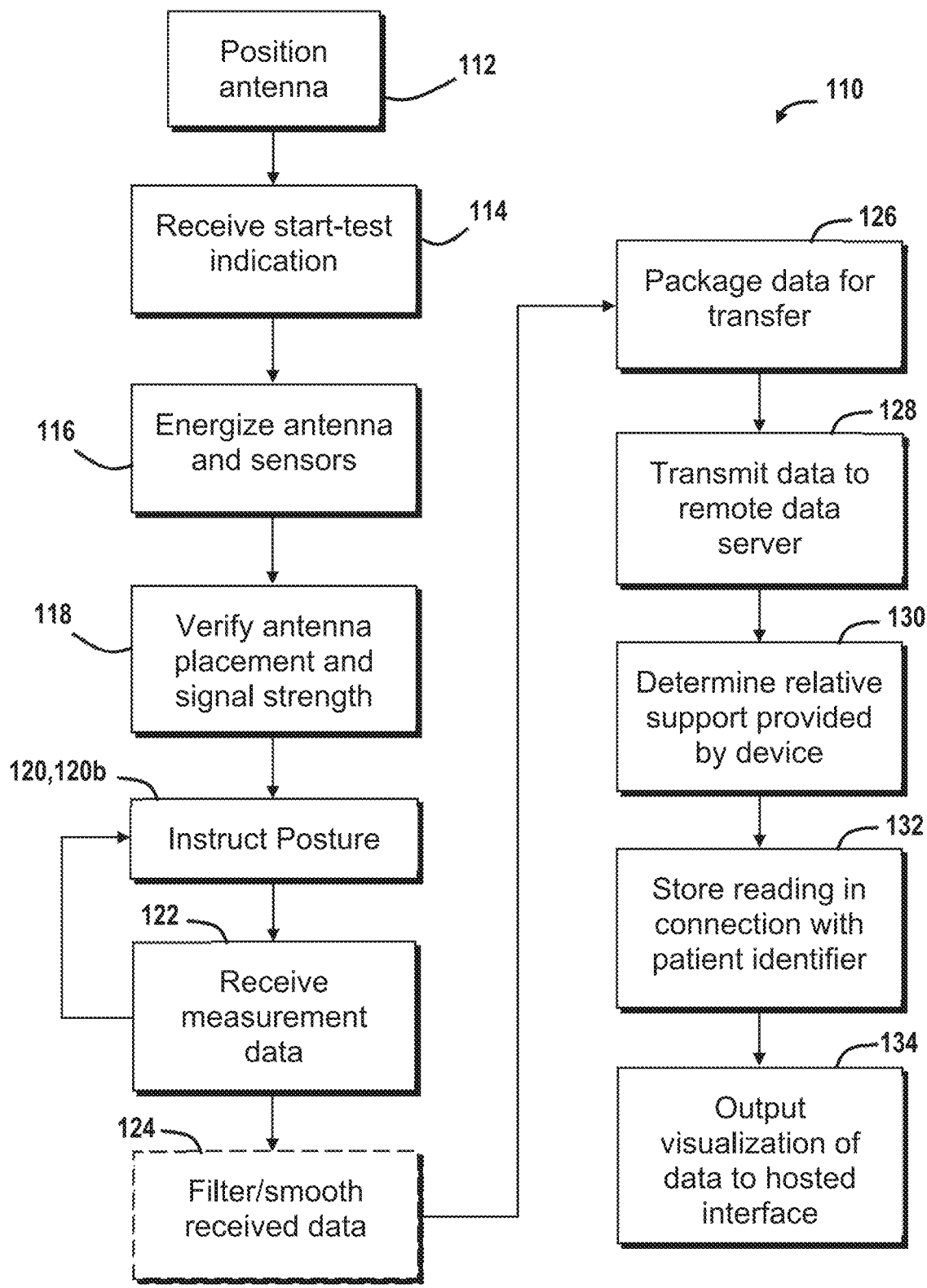
FIG. 6 is a schematic diagram of a method of acquiring and aggregating patient healing data from an implantable smart fixation device.

FIG. 6 schematically illustrates a method 110 of acquiring and aggregating patient healing data using the present system 10. The method 110 begins at 112 with the antenna 70 being positioned in contact with or outwardly adjacent to a skin surface of body. In some configurations, such as when using RFID communication protocols, the antenna 70 may be placed such that it is approximately centered above/radially outward from at least one implantable primary load sensor 52, and at least one implantable reference load sensor 54, where each load sensor 52, 54 is in direct physical communication with a bone plate 12 or other bone fixation device. One or more straps 73 or sleeves may be used to hold the antenna 70 in place during the test, such as by wrapping around a portion of the wearer's body. Once the antenna 70 is in place at 112 and secured to the wearer's body, the portable computing device 72 may receive an indication at 114 that the patient/user wishes to begin the test and begin acquiring strain data. This indication 114 may be received via the input device 90 and may comprise, for example, a physical or virtual button press.

Once the indication to begin has been received at 114, the processor 80 may energize the antenna 70 via the power transmission circuitry 78 (at 116), which may in turn energize and/or activate the sensors 52, 54. Following this, the processor 80 may examine the existence and/or strength of the data signal being returned from each sensor 52, 54 to determine if the device is operational and properly positioned (at 118). If the signal to noise ratio is too low (such as generally illustrated at 94 in FIG. 5), or if the sensor is returning an unexpected reading, then the processor 80 may instruct the user to reposition the antenna or seek further support. If the sensors are working well and returning an adequate signal, the processor 80 may then instruct the user, via the display 88, about how to position their body (at 120). For example, as shown in FIG. 5 at 96, the display 88 may illustrate a picture of a person sitting to indicate that the patient should be in a seated position. This position may be confirmed, for example, through the expiration of a countdown timer, actuation of a button by the user that confirms the posture, or automatically through orientation data acquired from an accelerometer or inertial measurement unit provided on the antenna 70.

Once the user's position has been verified (directly or indirectly), the processor 80 may receive measurement data from the load sensors 52, 54 by way of the antenna 70 and communication circuitry 76 (at 122). Following receipt, this data may optionally be filtered or smoothed (at 124) by the portable computing device 72 to remove communication or measurement noise, errant harmonics, and the like. Example filtering techniques may employ the use of low pass or band pass filtering techniques and/or data averaging techniques to remove noise within the signal. Further techniques may include various clipping or sampling strategies that are operative to isolate a subset of the total received signal with the least average or total variance (e.g., root mean squared (RMS) variance).

Once any on-board data processing is complete (if any such processing is desired), the processor 80 may package the strain data (at 126) from the load sensors 52, 54 (in raw and/or filtered/clipped form) together with a unique identifier corresponding to at least one of the subject's identity or the identity of the implantable smart fixation device 40 or the strain sensors mounted thereon. Packaging such data may include generating a digital file in memory that includes the sensor data in delimited form together with header or metadata information that includes the date/time of the reading(s), device data, environmental data, and/or subject/device identifying data. The packaged data/data file may then be transmitted (at 128) to the data server 20 via the wireless communication network 28 where it may then be aggregated and/or recorded in connection with the unique patient identifier (at 132).

The present system may be operatively configured to interpret the acquired strain data to determine an amount of relative support provided by the bone plate due to the fracture using the differing readings between the primary load sensor 52 and the reference load sensor 54 (at 130). In practice, such an analysis may be performed either using the processor 80 or by the data server 20. If the analysis is performed by the device processor 80, then the results of the analysis would be packaged together with the filtered or raw data and the unique identifier prior to transmission of the information.

In one configuration, the relative amount of support provided by the bone plate may be expressed as a ratio of a strain sensed by the primary load sensor 52 to a strain sensed by the reference load sensor. As the bone heals, this value would be expected to decrease toward 1.0 (accounting for varying biomechanical dynamics where strain may be non-uniform across the length of a bone). A ratio greater than 1.0 would suggest that the bone plate is carrying a greater amount of load across the fracture than at a point apart from the fracture.

In some embodiments, the processor 80 may further normalize a measurement or ratio taken during a load-bearing posture (e.g., a load-bearing ratio) with one taken at no load (e.g., a no-load ratio). For example, when monitoring a fracture in the femur, a load-bearing posture may involve the patient standing upright, whereas a no-load posture may involve the patient in a seated position. To accomplish this, the method 110 may repeat the instruction/measurement steps (generally at 120-124) while instructing the patient, via the display 88, to position themselves in a different body position (at 120b in FIG. 6 and graphically illustrated at 98 in FIG. 5). In one configuration, the first suggested body positioning would be a reference position where there is substantially no load on the fracture. The second position may then be a position where a load is applied to the fracture.

In one configuration, the above-referenced normalization may simply involve calculating the ratio of primary to reference strains as a ratio of changes in strain. Said another way, the system may calculate a delta increase in strain at the fracture from the no-load to the load-bearing posture, and then divide that value by a similarly calculated delta increase in strain at the reference location (i.e., from the no-load to the load-bearing posture). This normalization may remove anomalies in the ratio that may be caused by different baseline readings between the sensors. In one configuration, such as generally illustrated at 98 in FIG. 5, when instructing the load-bearing posture, the processor 80 may compare the strain from the reference sensor 54 in the load-bearing posture with the strain from that sensor in the no-load posture.

To ensure that a sufficient load is applied to the bone to achieve a meaningful data point, the processor 80 may monitor the absolute and/or delta strain at the fracture to ensure that it is above a predetermined threshold while in the instructed load-bearing posture. If the strain is below a threshold value, the processor 80 may instruct the wearer to apply greater load to the fractured bone (such as generally shown at 98 in FIG. 5). If the ratio or difference is above the threshold, the readings may be recorded with the confidence that the bone in the load-bearing posture is bearing a sufficient amount of load for the results to be meaningful.

In other embodiments, instead of taking a measurement during a static loading condition, the portable computing device 72 may instead instruct the patient (at 120) to engage in some dynamic movement. For example, the portable computing device 72 may instruct the patient to walk, perform certain stretches, or perform other functional activities such as standing from a seated position, climbing up stairs, or the like. In this configuration, instead of simply filtering and/or averaging the received strain readings to arrive at a single static strain value, the processor 80 may examine the strain readings over time to identify peak loading throughout the functional activity. These peak loading values/ratios may then be normalized against identified minimum loading values/ratios instead of requiring discrete load-bearing and no-load postures.

Figure 7:
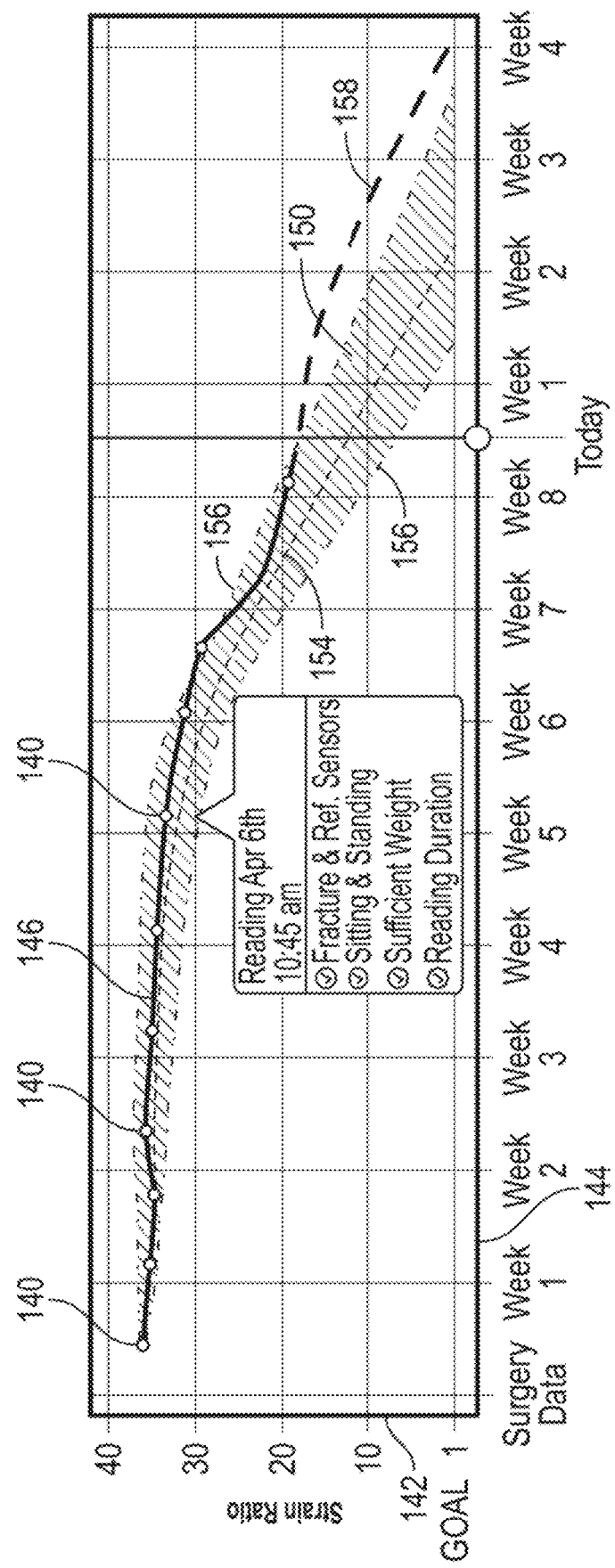
FIG. 7 is a schematic illustration of a patient-specific trendline drawn through a plurality of load ratio data points taken over time.

Once a support ratio is obtained, this value may similarly be recorded in connection with the subject's identifier. In one configuration, each patient may have a plurality of data points associated with their unique patient identifier. Each data point may represent a test result that is acquired at a different point in time. FIG. 7 schematically illustrates a plurality of patient data points 140, each representing an acquired, load ratio 142 over time 144. As shown in FIG. 7, from these plurality of data points 140, a trendline 146 may be constructed that represents a patient's healing progress over time.

Figure 8:
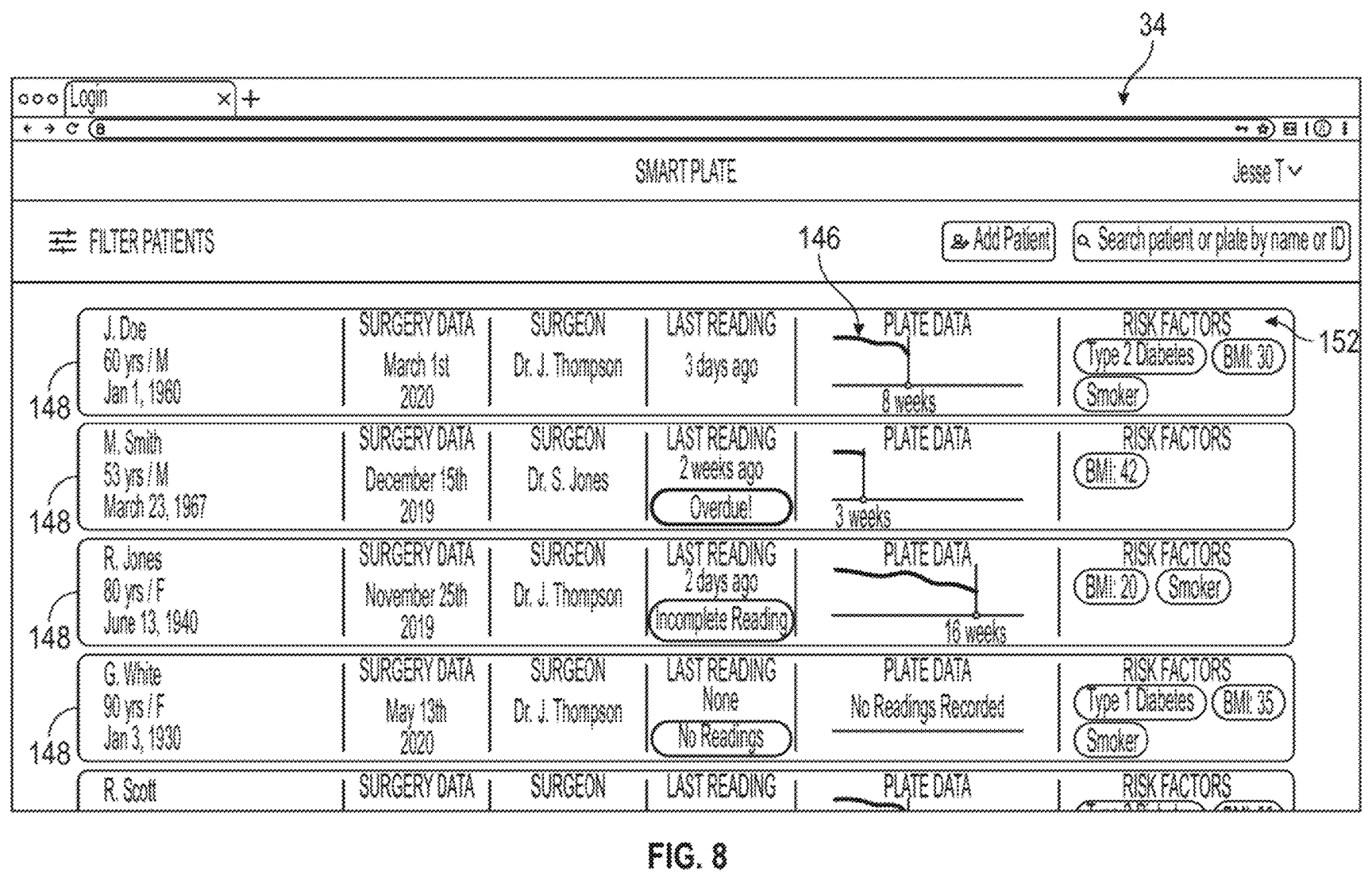

Upon receipt of a request from a user or medical professional 32 (at 134 in FIG. 6) the data server 20 may visually represent the aggregated patient data through a hosted user interface/physician interface 34, such as shown in FIG. 8. In one configuration, the physician interface 34 may be a web-based display that, for example, graphically illustrates the healing progress of one or more patients 148 through the display of acquired data points 140 and/or trendlines 146 over time 142. In one configuration, the physician interface 34 may include a summary screen, such as shown in FIG. 8, that enables the physician to quickly scan the progress and compliance of a number of patients that are each using the present system and periodically transmitting their respective patient data 24 to the data server 20. Selecting any one patient may transition the physician interface 34 from the summary screen to a more detailed graphical display of the trend for the selected patient, such as shown in FIG. 7.

In one configuration, as also shown in FIG. 7, the data server 20 may compute and display a patient specific trajectory range 150 within which the patient's actual trendline 146 is expected to fall within over time. In one configuration, the patient specific trajectory range 150 may be a statistical estimation based on one or more qualitative and/or quantitative attributes/metrics extracted from the patient's medical record or otherwise entered into the data server 20. These characteristics may include factors such as the nature and location of the fracture, the patient's height, weight, age, sex, metabolic profile, blood pressure, pre-existing conditions, complicating risk factors/comorbidities 152 (shown in FIG. 8), or other such factors that may impact healing. In some embodiments, the trajectory range 150 may be further influenced by empirical data taken from prior patients. For example, the data server 20 may maintain a machine learning model (e.g., a supervised or unsupervised learning model) in which experiential evidence drawn from prior patients serves to improve the predictive accuracy of the model for future patients. The patient specific trajectory range 150 may comprise a predicted trajectory 154 together with one or more confidence intervals 156 that diverge with the passage of time. In one configuration, the patient specific trajectory range 150 may be a static trajectory range 150 that is calculated as of the day that the bone is set (i.e., day 0) and not updated. By not continuously refining the model, the medical professional may understand whether the patient is healing as expected, or if there are unforeseen complications that need to be addressed.

In some embodiments, the data server 20 may further attempt to extrapolate a trajectory at each step (i.e., where the most recent data point is always day 0 and the prior trendline is an additional input into the model). This forward-looking trajectory 158 may provide advanced notice to the medical professional if the heading of the curve could be a cause for concern at a later date. For example, the forward-looking trajectory 158 in FIG. 7 is forecasting a slowed healing progression 1-2 weeks into the future that may be outside the bounds of what is expected. This prediction may alert the physician that something might be complicating the healing processes and may warrant further investigation. Further, in one configuration, the data server 20 may provide an alert via the physician interface 34 if one of the data points or the forward-looking healing trajectory is outside of the confidence interval. In this manner, the more frequent monitoring provided by the present system, together with the enhanced data visualization and predictive analytics may result in a more complete understanding of how the patient is healing with respect to reasonable expectations. This enhanced understanding may enable the physician to intervene at an earlier stage should complications begin to occur. Likewise, this data may also serve to provide guidance on a recommended physical therapy treatment and recommended overall patient activity level.

In one configuration, in addition to being displayed to the physician via the hosted interface 34, the recorded patient data points 140, patient specific trajectory range 150, forward looking trajectory 158, and/or one or more qualitative summaries may also be displayed to the patient via the display 88. In doing so, the healing process may be gamified, for example, by celebrating or providing virtual rewards when certain milestones are achieved. Likewise, the portable computing device may either automatically, or under the remote guidance/input from the physician, convey tips or behavioral recommendations to aid the patient in maintaining compliance with the prescribed course of treatment.

Figure 9:
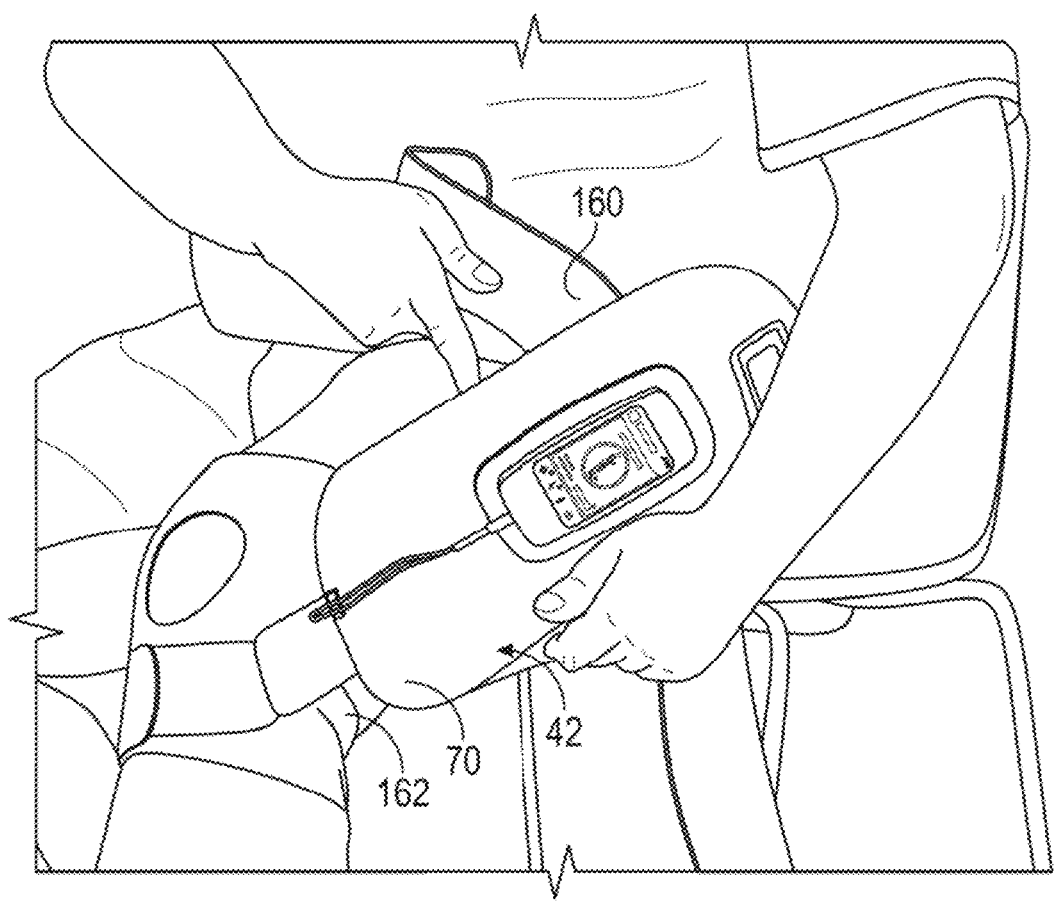
FIG. 9 is a schematic side perspective view of an external wireless reader being secured to the upper thigh of a patient.

FIG. 9 schematically illustrates one manner of affixing the external wireless reader 42 and/or antenna 70 to the body of the user, and more specifically to the upper thigh as would be needed with a femoral fracture. In such a use, affixment to the body has presented challenges since the muscles of the upper leg change in thickness based on the posture of the patient. For example, as the patient transitions from sitting to standing, the circumference of their thigh noticeably decreases. If not accounted for, this decrease in leg circumference may result in the external wireless reader 42 slipping downward from its intended positioning. To discourage this slippage, in one embodiment the external wireless reader 42 may include one or more elastic straps 160 that are configured to be secured around a circumference of the body of the patient. These elastic straps 160 preferably obtain a tension fit such that they are elastically stretched around the patient's limb while applying a compressive force against the patient's skin. In some embodiments, the external wireless reader 42 may further include one or more braces 162 that are configured to be secured around a joint of the fractured bone. For example, in a fracture of the femur, the external wireless reader 42 may include a knee brace 164 that is configured to extend around the patient's knee. The antenna 70 may then be rigidly positioned relative to this brace 162. Such a design may be advantageous because the circumference of joints does not significantly change based on posture, and similarly, the position of the fracture relative to the joint also remains constant. This design would not rely solely on a constricting elastic strap to maintain positioning, where sole reliance on an elastic strap may prove to be uncomfortable by some patients. In alternate embodiments, a hip brace or belt could be used in place of the knee brace 162.

The present technology represents an advancement in the ability for a physician to more actively monitor the healing progress of an internally fixated bone fracture. Using this increased quantitative monitoring that is particularly suited for remote supervision/telemedicine, the physician may have a more complete picture of how the bone is ossifying than was available with existing practices. With this information, the physician may more actively tailor physical therapy regimens, counsel the patient on acceptable activity levels or diet, or may even take proactive intervention steps if such are required. Due to the generally slow speed at which bones heal, the present device may not need to be worn continuously. Instead, the external wireless reader 42 may be more akin to a blood pressure cuff, where it only needs to be worn during the test (which may only be required a couple/few times each week).

Further aspects and advantages of the present technology are provided in the following clauses:

Clause 1. A patient monitoring system for monitoring the ossification of an internally fixated fracture in a bone of a subject, the system comprising: an implantable fixation device operative to be affixed to the bone, the fixation device including: a bone plate configured to be secured to the bone on opposing sides of the fracture; a primary load sensor provided on the bone plate at a first location that is operative to be positioned directly adjacent to the fracture, the primary load sensor including: a first strain sensor operative to monitor an amount of strain in the bone plate at the first location (Primary Strain); and communication circuitry operative to transmit a first wireless signal indicative of the amount of Primary Strain; a reference load sensor provided on the bone plate at a second location that is spaced apart from the first location, the reference load sensor including: a second strain sensor operative to monitor an amount of strain in the bone plate at the second location (Reference Strain); and communication circuitry operative to transmit a second wireless signal indicative of the amount of Reference Strain; an external wireless reader including an antenna, a processor, and a wireless communications radio, wherein the processor is configured to: receive the first and second wireless signals via the antenna; transmit a signal to a data server over a wireless communication network using the wireless communication radio, the signal indicative of the amount of Primary Strain, the amount of Reference Strain, and further including a unique identifier corresponding to at least one of the subject or the implantable fixation device.

Clause 2. The patient monitoring system of clause 1, further comprising the data server in digital communication with the external wireless reader; wherein at least one of the processor or the data server is configured to: determine an amount of relative support provided by the bone plate as a result of the fracture using the received indication of the Primary Strain and the received indication of the Reference Strain; and store the determined amount of relative support in non transitory memory in communication with at least one of the processor or the data server.

Clause 3. The patient monitoring system of clause 2, wherein the processor or data server is configured to determine the amount of relative support provided by the bone plate by computing a ratio of the Primary Strain to the Reference Strain.

Clause 4. The patient monitoring system of clause 3, wherein the processor is further configured to: prompt the subject to position the bone in a first no-load posture and separately to position the bone in a second load-bearing posture; determine an amount of Primary Strain in each of the first no-load posture and the second load-bearing posture; determine an amount of Reference Strain in each of the first no-load posture and the second load-bearing posture; and wherein the at least one of the processor or data server is configured to determine the amount of relative support provided by the bone plate by computing a ratio of the difference in Primary Strain between the no-load posture and the load-bearing posture to the difference in Reference Strain between the no-load posture and the load-bearing posture.

Clause 5. The patient monitoring system of clause 4, wherein the external wireless reader further includes a display, and wherein the processor is configured to prompt the subject to position the bone in the first no-load posture and separately in the second load-bearing posture via the display.

Clause 6. The patient monitoring system of clause 5, wherein the processor is configured to prompt the subject, via the display, to apply additional load to the bone if the Primary Strain in the load-bearing posture is less than a predetermined minimum threshold amount of strain.

Clause 7. The patient monitoring system of any of clauses 4-6, wherein the at least one of the processor or data server is configured to determine the amount of relative support provided by the bone plate only if the Primary Strain in the load-bearing posture exceeds a predetermined minimum threshold amount of strain.

Clause 8. The patient monitoring system of any of clauses 1-7, wherein the external wireless reader further includes an inductive charging circuit that is operative to power each of the primary load sensor and reference load sensor via a magnetic field transmitted from the antenna.

Clause 9. The patient monitoring system of clause 8, wherein the external wireless reader comprises a wearable component in wired communication with a display device via a tether; and wherein the wearable component comprises the antenna provided within a carrier having at least one strap configured to extend around a portion of the subject.

Clause 10. The patient monitoring system of clause 9, wherein the wearable component further includes the processor.

Clause 11. The patient monitoring system of any of clauses 9-10, wherein the fabric carrier is further secured to a brace that is operative to extend around a joint of the subject.

Clause 12. The patient monitoring system of any of clauses 1-11, wherein the antenna has a length and wherein the length of the antenna is greater than a spacing between the first location and the second location.

Clause 13. A method of monitoring bone fracture ossification from a plurality of subjects, the method comprising: receiving, via a wireless communication network, a plurality of data sets from a plurality of subjects, each data set representing a plurality of strain measurements taken from a smart fixation device secured to a bone of a subject across a fracture, the plurality of strain measurements including at least a first strain measurement indicative of an amount of load carried by the fixation device across the fracture (Primary Strain), and at least a second strain measurement indicative of an amount of load carried by the fixation device at solid bone (Reference Strain); calculating a ratio of an amount of Primary Strain to an amount of Reference strain for each of the plurality of data sets. storing each data set and each calculated ratio in nonvolatile memory in connection with the date and time of the strain measurements and with a patient identifier representing the source of the measurement; and providing a physician interface to graphically illustrate a change in the ratio from each of a plurality of different subjects over time.

Clause 14. The method of clause 13, further comprising maintaining a machine learning predictive model that generates a predicted patient specific healing trajectory for each subject, the patient specific healing trajectory including a predicted trajectory and a confidence interval that represents a likely course of healing progression beginning at the time of bone fixation, the method further including overlaying the plurality of data sets for a subject on a graphical representation of the predicted patient specific healing trajectory within the physician interface; and wherein the machine learning predictive model is refined using at least a subset of the received data sets and a plurality of secondary factors including at least two of: a nature and location of the fracture, the subject's height, weight, age, sex, metabolic profile, blood pressure, pre-existing conditions, complicating risk factors, or comorbidities.

Clause 15. The method of clause 14, further comprising: computing a forward-looking healing trajectory for each subject extending forward in time from the most recently acquired data set for that subject; and overlaying the forward-looking healing trajectory on the graphical representation of the predicted patient specific healing trajectory.

Clause 16. The method of clause 15, further comprising providing an alert via the physician interface if one of the data sets or the forward-looking healing trajectory is outside of the confidence interval.

Clause 17. A method of acquiring bone ossification data from an implantable smart fixation device provided within a subject, the method including: energizing an extracorporeal antenna to generate an alternating magnetic field and inductively energize a plurality of load sensors provided in contact with a bone plate secured to a bone across a fracture; receiving, via the extracorporeal antenna, a wireless data signal from each of the plurality of load sensors, the wireless data signal indicative of an amount of strain experienced by the bone plate; identifying a representative strain value from each wireless data signal; determining an amount of relative load carried by the bone plate across the fracture by dividing a first strain value indicative of an amount of strain experienced by the bone plate at the fracture by a second strain value that is indicative of an amount of strain experienced by the bone plate apart from the fracture.

Clause 18. The method of clause 17, further comprising: prompting the subject, via an electronic display, to position the bone or the subject's body in a first, no-load posture; and prompting the subject, via the electronic display, to position the bone or the subject's body in a second, load-bearing posture, wherein the bone plate experiences at least a predetermined minimum amount of strain in the load-bearing posture; and wherein each of the first strain value and second strain value comprises a difference between an amount of strain measured in the load-bearing posture and the no-load posture.

Clause 19. The method of clause 18, further comprising providing an alert to the subject if the amount of strain in the load-bearing posture is less than the predetermined minimum amount of strain.

Benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are expressly stated in such claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

Additional embodiments of the external wireless reader are provided in the Appendix, which is submitted herewith.

What is claimed is:

1. A patient monitoring system for monitoring the ossification of an internally fixated fracture in a bone of a subject, the system comprising:
    an implantable fixation device operative to be affixed to the bone, the fixation device including:
        a bone plate configured to be secured to the bone on opposing sides of the fracture;
        a primary load sensor provided on the bone plate at a first location that is operative to be positioned directly adjacent to the fracture, the primary load sensor including:
            a first strain sensor operative to monitor an amount of strain in the bone plate at the first location (Primary Strain); and
            first communication circuitry operative to transmit a first wireless signal indicative of the amount of Primary Strain;
        a reference load sensor provided on the bone plate at a second location that is spaced apart from the first location, the reference load sensor including:
            a second strain sensor operative to monitor an amount of strain in the bone plate at the second location (Reference Strain); and
            second communication circuitry operative to transmit a second wireless signal indicative of the amount of Reference Strain; and
    an external wireless reader including an antenna, a processor, and a wireless communications radio, wherein the processor is configured to:
        receive the first and second wireless signals via the antenna; and
        transmit a signal to a data server over a wireless communication network using the wireless communication radio, wherein the signal includes an indication of the amount of Primary Strain, the amount of Reference Strain, and a unique identifier corresponding to at least one of the subject or the implantable fixation device;
    wherein at least one of the processor or the data server is configured to:
        determine an amount of Primary Strain in each of a no-load posture and a load-bearing posture;
        determine an amount of Reference Strain in each of the no-load posture and the load-bearing posture; and
        determine the amount of relative support provided by the bone plate by computing a ratio of the difference in Primary Strain between the no-load posture and the load-bearing posture to the difference in Reference Strain between the no-load posture and the load-bearing posture.

2. The patient monitoring system of claim 1, further comprising the data server, wherein the data server is in digital communication with the external wireless reader;
    wherein at least one of the processor or the data server is configured to:
        determine an amount of relative support provided by the bone plate as a result of the fracture using the received indication of the Primary Strain and the received indication of the Reference Strain; and
        store the determined amount of relative support in non transitory memory in communication with at least one of the processor or the data server.

3. The patient monitoring system of claim 2, wherein at least one of the processor or data server is configured to determine the amount of relative support provided by the bone plate by computing a ratio of the Primary Strain to the Reference Strain.

4. The patient monitoring system of claim 3, wherein the processor is further configured to:
    prompt the subject to position the bone in the no-load posture and separately to position the bone in the load-bearing posture.

5. The patient monitoring system of claim 4, wherein the external wireless reader further includes a display, and wherein the processor is configured to prompt the subject to position the bone in the no-load posture and separately in the load-bearing posture via the display.

6. The patient monitoring system of claim 5, wherein the processor is configured to prompt the subject, via the display, to apply additional load to the bone if the Primary Strain in the load-bearing posture is less than a predetermined minimum threshold amount of strain.

7. The patient monitoring system of claim 4, wherein the at least one of the processor or data server is configured to determine the amount of relative support provided by the bone plate only if the Primary Strain in the load-bearing posture exceeds a predetermined minimum threshold amount of strain.

8. The patient monitoring system of claim 1, wherein the external wireless reader further includes an inductive charging circuit that is operative to power each of the primary load sensor and reference load sensor via a magnetic field transmitted from the antenna.

9. The patient monitoring system of claim 8, wherein the external wireless reader comprises a wearable component in wired communication with a display device via a tether; and wherein the wearable component comprises the antenna provided within a carrier having at least one strap configured to extend around a portion of the subject.

10. The patient monitoring system of claim 9, wherein the wearable component further includes the processor.

11. The patient monitoring system of claim 9, wherein the carrier is further secured to a brace that is operative to extend around a joint of the subject.

12. The patient monitoring system of claim 1, wherein the antenna has a length, and wherein the length of the antenna is greater than a spacing between the first location and the second location.

13. The patient monitoring system of claim 1, wherein the antenna has a width, and wherein the width of the antenna is between about 12 cm and 20 cm.

* * * * *